United States Patent [19]

Schallhorn

[11] Patent Number: 6,120,467
[45] Date of Patent: Sep. 19, 2000

[54] SPINAL CORD SIMULATION SYSTEMS WITH PATIENT ACTIVITY MONITORING AND THERAPY ADJUSTMENTS

[75] Inventor: Rick Schallhorn, Lake Elmo, Minn.

[73] Assignee: Medtronic Inc., Minneapolis, Minn.

[21] Appl. No.: 09/070,348

[22] Filed: Apr. 30, 1998

[51] Int. Cl.[7] .................................................. A61B 5/00
[52] U.S. Cl. .............................. 600/595; 607/46; 607/116
[58] Field of Search ................................ 607/46, 30, 19, 607/32, 116, 62, 60; 600/595

[56] References Cited

U.S. PATENT DOCUMENTS

| | | |
|---|---|---|
| 5,370,672 | 12/1994 | Fowler et al. . |
| 5,555,891 | 9/1996 | Eisenfeld . |
| 5,562,711 | 10/1996 | Yerich et al. . |
| 5,593,431 | 1/1997 | Sheldon ................................... 607/19 |
| 5,662,689 | 9/1997 | Elsberry et al. . |
| 5,702,429 | 12/1997 | King .......................................... 607/46 |
| 5,720,770 | 2/1998 | Nappholz et al. ........................ 607/30 |

FOREIGN PATENT DOCUMENTS

| | | |
|---|---|---|
| 0625383 | 5/1993 | European Pat. Off. . |
| 9222245 | 12/1992 | WIPO . |
| 9629007 | 9/1996 | WIPO . |

*Primary Examiner*—Max Hindenburg
*Assistant Examiner*—Brian Szmal
*Attorney, Agent, or Firm*—Medtronic, Inc.

[57] ABSTRACT

A patient activity level recorder and a patient therapy adjustment recorder are provided to obtain an historical representation of patient activity levels and therapy changes in the form of profiles which are stored for later retrieval. The patient activity level profile and the therapy adjustment profile may be used to objectively interpreting subjective patient information. The activity level recorder may include an accelerometer, the output of which is processed by a signal processor, programmed to interpret the sensor raw signal as one of a plurality of predetermined activity levels. In a preferred embodiment, data for rest, moderate and vigorous activity levels for each day in a recording period are stored for later retrieval and use by a physician, or possible by the patient where therapy is self-administered. The therapy adjustment recorder may include a processor for interpreting signals from a patient control interface to a pulse generator of a spinal chord stimulation system.

13 Claims, 4 Drawing Sheets

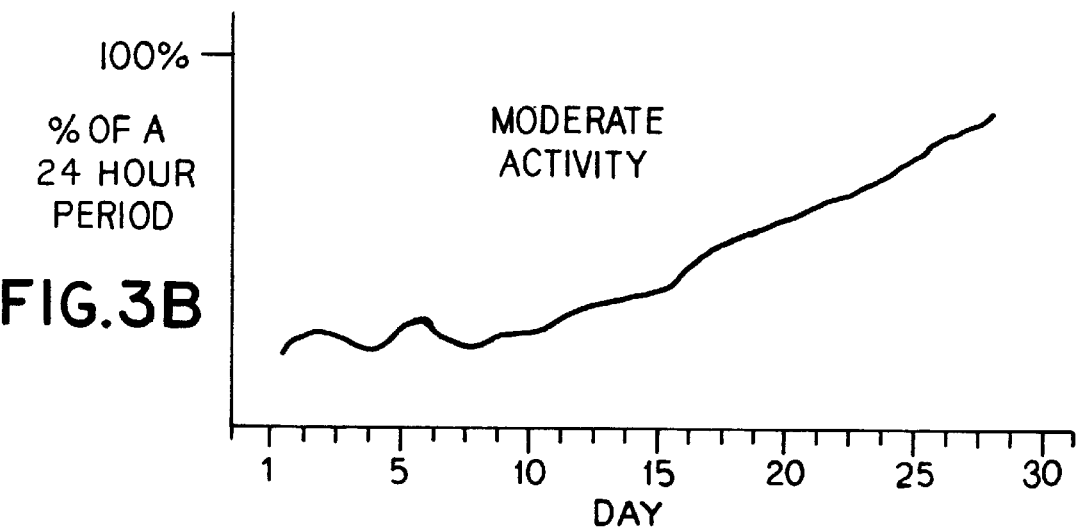
FIG. 3A
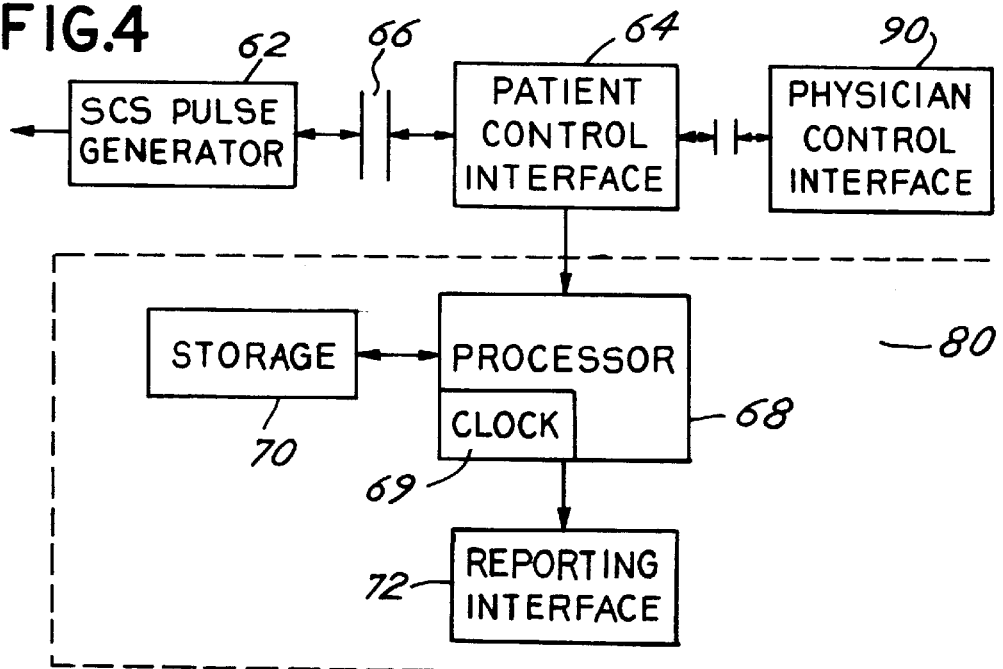
FIG. 3B
FIG. 4

SPINAL CORD SIMULATION SYSTEMS WITH PATIENT ACTIVITY MONITORING AND THERAPY ADJUSTMENTS

FIELD OF THE INVENTION

This invention relates to systems for obtaining objective patient data, for example, by monitoring patient physiologic and metabolic activity and adjustments to patient therapy. More particularly, the invention relates to a system and method for obtaining objective information about patient activity levels, activity patterns and patient-activated changes in Spinal Cord Stimulation (SCS) therapy and using such objective information to interpret subjective patient responses to physician inquiry.

BACKGROUND OF THE INVENTION

SCS therapy is a relatively recent development in which electrical stimulation is applied to the central nervous system in the spinal cord area for the relief of pain of the trunk and/or limbs. Presently, there exist no known techniques for objectively determining the efficacy of an SCS system. Typically, efficacy determinations for SCS systems rely on empirical methods which are based on information conveyed from the patient to clinicians. For example, to assess efficacy a physician will interview a patient and ask simple questions relative, for example, to the level of pain that the patient is or has been experiencing after SCS has been implemented.

Currently, the practice of adjusting or optimizing post-implantation parameters in SCS systems relies exclusively on patient-reported feedback. Patient reporting is subject to the patient's own perception of symptoms. This prevents objective determinations of symptomatic conditions and leaves diagnostic procedures prone to inappropriate assumptions about the existing or potential efficacy of SCS in a given patient. To illustrate the problem, one can imagine a patient being treated with SCS who experiences significant pain reduction. As a result of the reduction in pain, the patient becomes more active, and takes part in day-to-day activities that were not undertaken before SCS treatment. That increase in activity actually causes the patient to experience more pain which may not necessarily be due to the condition treated with SCS, but instead may be the result of the heightened activity level. When asked whether pain has decreased, the patient may very well respond that it has not, even though the SCS may actually be mitigating the pain level. Thus, present efficacy evaluation techniques do not allow for a objective qualification of patient reported data.

It would therefore be desirable to provide a system which enables objective interpretation of subjective information regarding the efficacy of an SCS system. In particular, it would be desirable to provide a system which permits storage and retrieval of an historical representation of objective patient data, including patient activity levels and therapy adjustments to provide a physician with an objective reference to subjective patient information.

SUMMARY OF THE INVENTION

The invention achieves the aforementioned objectives by providing, according to a preferred embodiment, a system for monitoring and obtaining an historical representation or profile of the activity level and/or therapy adjustments of a patient. An activity level recorder, which is preferably incorporated into the structure of an SCS implantable generator, senses, according to output from an accelerometer and possibly other sensors, the amount of activity a patient is experiencing. The activity recorder is provided with a processor which is programmed to translate and categorize sensor output data into a number of predetermined activity categories. A patient activity level profile includes data about the activity undertaken by the patient in each of the different activity categories and is stored for later retrieval. A physician may then retrieve and review the activity level profile use it to objectively interpret subjective information obtained by interviewing the patient.

According to a preferred embodiment, activity levels for rest, moderate and vigorous activity are stored in daily profiles, which provide values for the amount of time that a patient has experienced each respective activity level. A physician viewing the daily profiles may determine whether a particular day included a significant amount of vigorous activity, for example, or whether a particular day was generally sedentary. Thus, an advantage provided by the present invention is that information obtained by interview regarding pain experience for a particular day may be objectively interpreted with regard to the activity level for that day or preceding days.

According to another feature of the invention, a therapy adjustment recorder is provided for storing one or more profiles representing the type and time of various patient therapy adjustments. Such adjustments may include adjustments to the pulse width, frequency and amplitude of an SCS signal. The patient therapy adjustment profiles may be stored in the therapy adjustment recorder for later retrieval by a physician. Therapy adjustment profiles provide another objective standard by which physicians may evaluate subjective patient data.

Other objects, advantages novel features, and the further scope of applicability of the present invention will be set forth in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings, in which like numbers refer to like parts throughout:

FIGS. 3A and 3B are illustrations of activity level profiles according to a preferred embodiment of the invention;

FIG. 4 is a schematic illustration of a therapy adjustment recorder for obtaining a therapy adjustment profile according to a preferred embodiment of the present invention.

DESCRIPTION OF THE PREFERRED EMBODIMENTS

Figure 1:
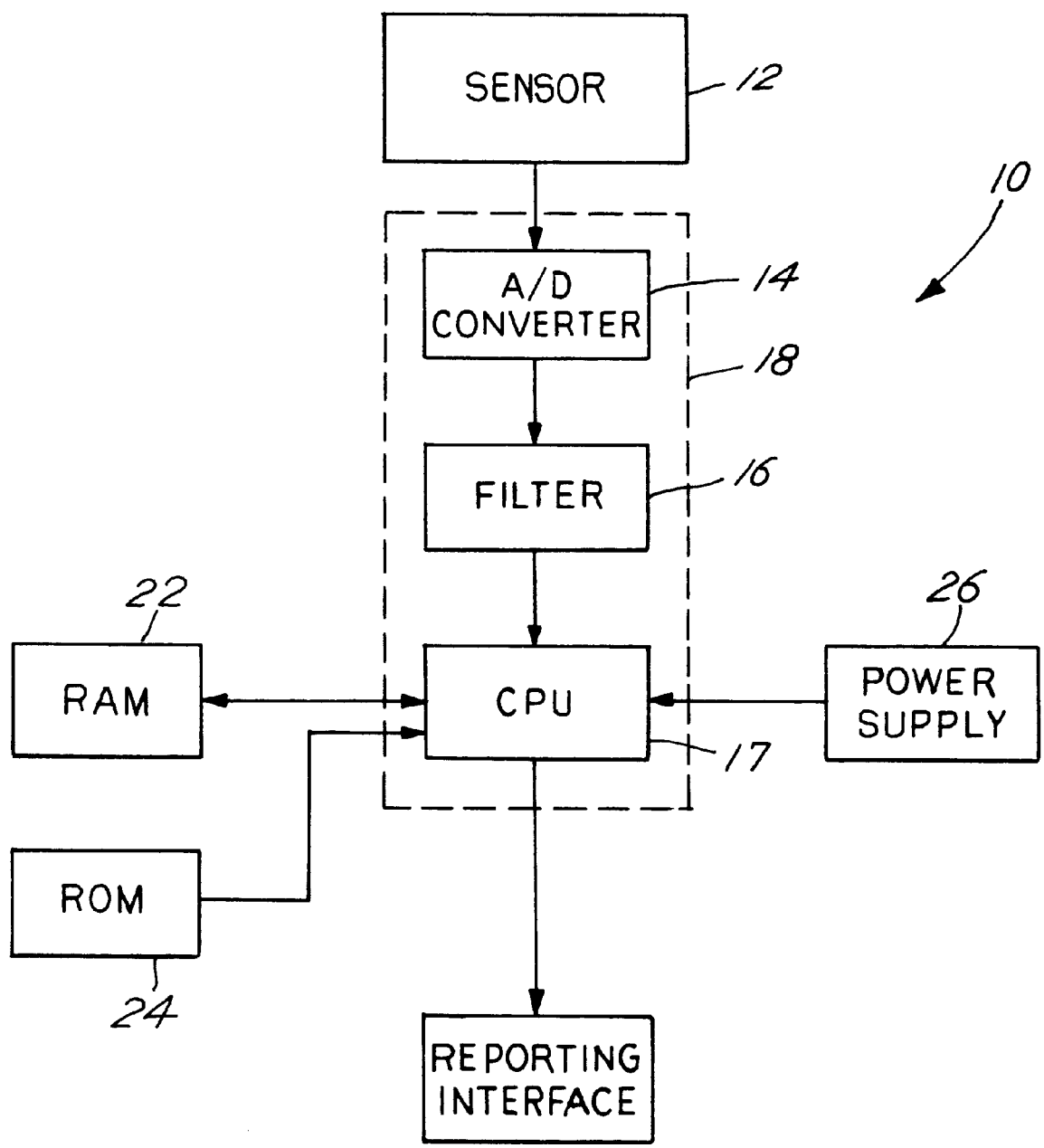
FIG. 1 is a block diagram of a device for obtaining a historical representation of patient activity levels according to a preferred embodiment of the invention.

FIG. 1 depicts in block diagram form an activity level recorder 10 for obtaining an historical representation of patient activity levels according to a preferred embodiment of the present invention. In the presently preferred embodiment of the invention, a sensor 12 is provided for generating a signal corresponding to activity undertaken by the patient. Sensor 12 may utilize a piezoelectric accelerometer for measuring changes in movement of the patient, patient's limbs or both. Preferably, sensor 12 is installed as an accelerometer mounted on the electronic circuit board inside of an implantable SCS generator.

Sensor 12 provides a raw electrical signal to a signal processor 18, which may include an analog-to-digital (A/D) converter 14 for converting the analog raw signal from sensor 12 into digital form, a filter 16, which may be a bandpass filter, for screening background noise from the sensor output signal, and a central processing unit (CPU) 17 for executing a sequence of processing instructions stored in RAM 22 and/or ROM 24 in a manner described below. It will be recognized that A/D converter 14 and filter 16 may be interchanged to obtain desired signal processing characteristics. CPU 17 is provided with an internal clock and calendar maintaining temporal orientation with respect to the processing of the sensor output signal. A power supply 26 is provided, preferably in the form of a battery, for supplying electrical energy to CPU and other system components which require it.

Those of ordinary skill will recognize that the invention contemplates alternative devices for sensing patient activity. For example, sensors which give a reading of certain metabolic activity could be substituted for or used in conjunction with the accelerometer. Conventional devices for sensing heart rate, respiration and body temperature, for example, could be employed to replace or augment the data output of sensor 12.

Figure 2:
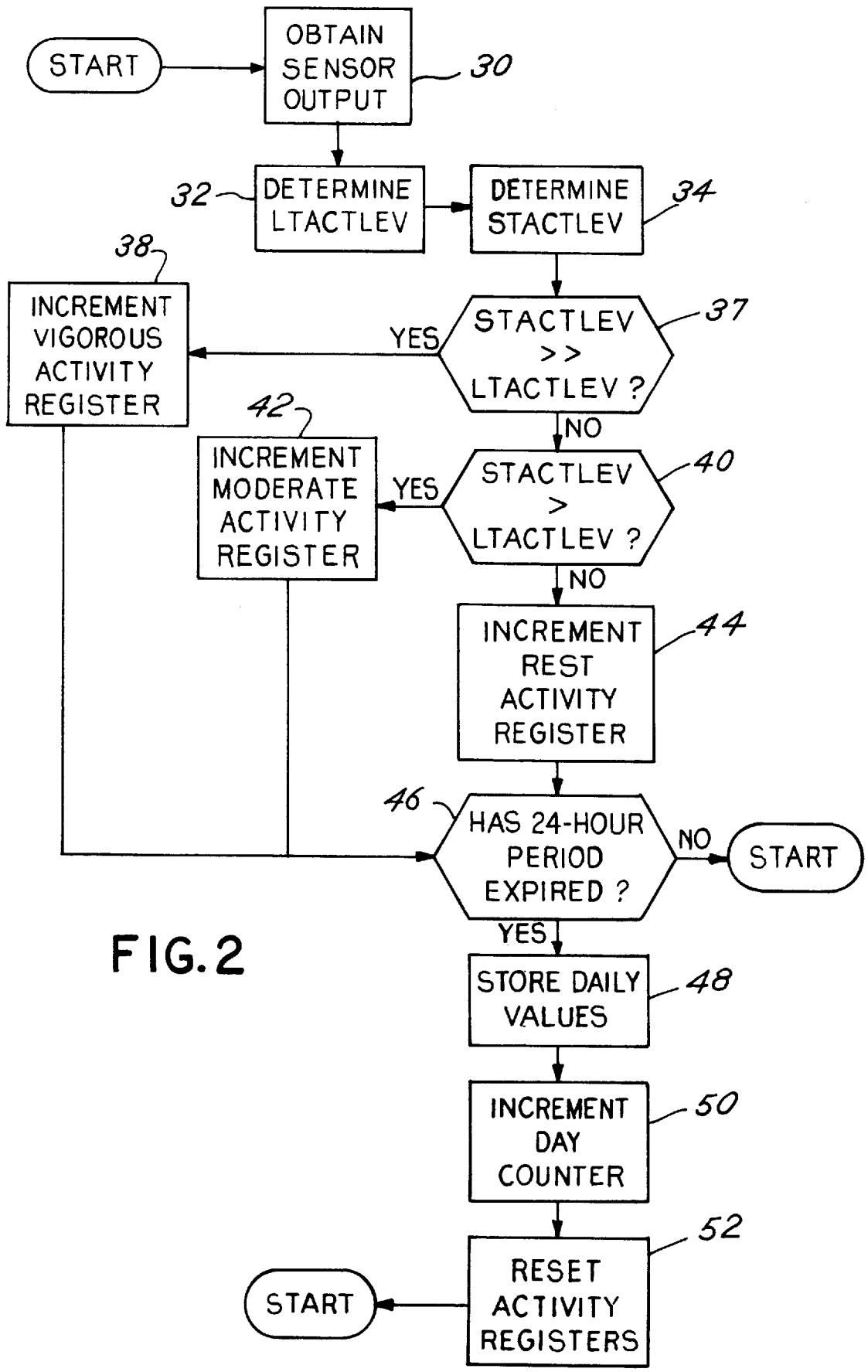
FIG. 2 is a flow diagram illustrating the steps of a process for generating patient activity level profiles according to a preferred embodiment of the invention.

FIG. 2 illustrates a flow diagram depicting the process steps accomplished by signal processor 18. It will be recognized by those of ordinary skill in the art that FIG. 2 represents an iterative process which may be executed many times per second or may be executed, for example, once every 10 seconds. At state 30, the current value of the sensor output signal is obtained by the signal processor 18. At state 32, a long-term average value for patient activity level, LTACTLEV is obtained. The value for LTACTLEV is computed by time-averaging the sensor output signal level over a time period corresponding preferably from one to four hours. As will be recognized, the process depicted in FIG. 2 would have to be initially executed for such a duration in order to determine the value of LTACTLEV. For each iteration, a running value of LTACTLEV may be determined by adding the value corresponding to the sensor output signal to a running sum of previous values over the four-hour interval and dividing that sum by the total number of processor clocking intervals corresponding to four hours.

At state 34, a short-term value for patient activity level STACTLEV is determined. STACTLEV is computed by time-averaging the sensor output signal level over a time period corresponding preferably to between 2 and 60 seconds. At state 37, a comparison is made to determine the relative values of STACTLEV and LTACTLEV. If it is determined that STACTLEV is much greater than LTACTLEV, for example, if STACTLEV exceeds LTACTLEV by a factor of 3, the signal processor branches to step 38. At step 38, a vigorous activity register, which may be defined as a location in RAM 22, is incremented with a time value corresponding to the clocking cycle of the depicted process. For example, if the process is programmed to occur at one-second intervals, then the vigorous activity register would be incremented by a value of one.

If the condition defined in step 37 is not met, the process continues to step 40 to determine if the sensor output signal corresponds to moderate activity level. At step 40, a determination is made as to whether STACTLEV exceeds LTACTLEV by, for example a factor of 2. If so, the process branches to state 42 where a moderate activity register is incremented. If the condition defined in step 40 is not met, the process continues to step 44 where, logically, the sensor output level must correspond to a resting condition and a rest activity register is incremented.

As shown in FIG. 2, each of states 38, 42 and 44 branch to a decision block 46 where a determination is made as to whether a 24-hour daily period has expired. Such a determination may be implemented, for example, by a running counter the value of which is checked at state 46 to determine if it corresponds to a 24-hour period. If it is determined that the daily clock has not expired, the process returns to state 30 for another iteration. However, if it is determined at state 46 that the 24 hour clock as expired, then the process branches to state 48 where daily values are stored in appropriate locations in RAM 22. The daily values for the vigorous and moderate activity levels and the rest activity level will correspond to the values stored in the respective registers. Thus, state 48 may be implemented by simply reading the value of the activity registers and writing that value to an assigned memory location corresponding to a particular day.

The process proceeds to state 50 where the day counter is incremented to signify the start of a new 24-hour period. Appropriately, the three activity level registers described above are reset to zero values at state 52 and the process returns to state 30 to begin monitoring activity levels for the next day.

FIG. 3A illustrates a patient activity level profile that may be stored in RAM 22 and later retrieved in a manner to be described below. The data may be stored in the form of a matrix which is visualized in the form of a table 50 that contains corresponding activity levels for each day of monitoring. For example, DAY 1 is assigned corresponding values for rest, moderate and vigorous activity levels of 14, 8 and 2 hours. DAY 2 corresponds to respective values of 20.3, 3.7 and zero. Referring again to FIG. 1, a reporting interface 26 is provided to CPU 17 to enable retrieval of the patient activity level profile stored in RAM 22. Reporting interface 26 may be provided in the form of an input/output bus or serial port, the details of which are well known to those of ordinary skill in the art. It will be recognized by those of ordinary skill that the number of activity categories may be varied such that, for example, five activity categories instead of three are provided. Similarly, while daily reporting intervals are described with respect to FIG. 3A, the duration and number of reporting intervals may be varied.

FIG. 3B illustrates another form of an historical representation of patient activity level data that may be stored in RAM 22. Here, a curve is represented for a 60-day interval for one of the activity level categories, in this case, moderate activity, as a percentage of daily activity. Such an activity level profile provides a physician with a readily-apparent indication of activity trends.

FIG. 4 illustrates a block diagram of a therapy adjustment recorder according to a preferred embodiment of the invention. Several commercially available SCS systems have functions that allow the patient to alter the parameters characterizing the therapy delivered to the patient. For example, the ITREL3 system manufactured by Medtronic, Inc. of Minneapolis, Minn., permits patient altering of the pulse frequency, pulse amplitude and pulse width in an SCS system. Settings are altered via hand-held radio frequency which communicates via telemetry with an implanted SCS pulse generator. Such a system is schematically represented in FIG. 4 along with the therapy adjustment profile generator according to a preferred embodiment of the present invention. SCS generator 62 is in electrical communication with an implanted lead (not shown) for delivering electrical stimulation to excitable tissue in the spinal dura. Through a radio frequency link 66, SCS generator 62 communicates with a patient control interface 64 for permitting a patient to adjust various parameters of the electrical stimulation applied to the excitable tissue. In accordance with the present invention, a therapy adjustment profile generator 80 comprises a data bus 82 which conveys data indicating the various parameters to a processor 68 which includes an internal clock 69 and timekeeping functions. Time and parameter data are periodically stored in storage 70 which is a memory device. Thus, particular parameter settings and changes therein may be correlated with particular times and days to form a therapy adjustment profile stored in storage 70. Processor 68 operates according to pre-programmed instructions to permit on-demand exporting of the therapy adjustment profile and retrieval by a physician. Once the information is stored in storage 70, the patient control interface 64 can send that information via RF to a physician control interface 90. This instrument can then display or print the information in several different formats. Reporting interface 72 provides an interface to processor 68 for enabling retrieval of a stored patient activity level profile.

Figure 5:
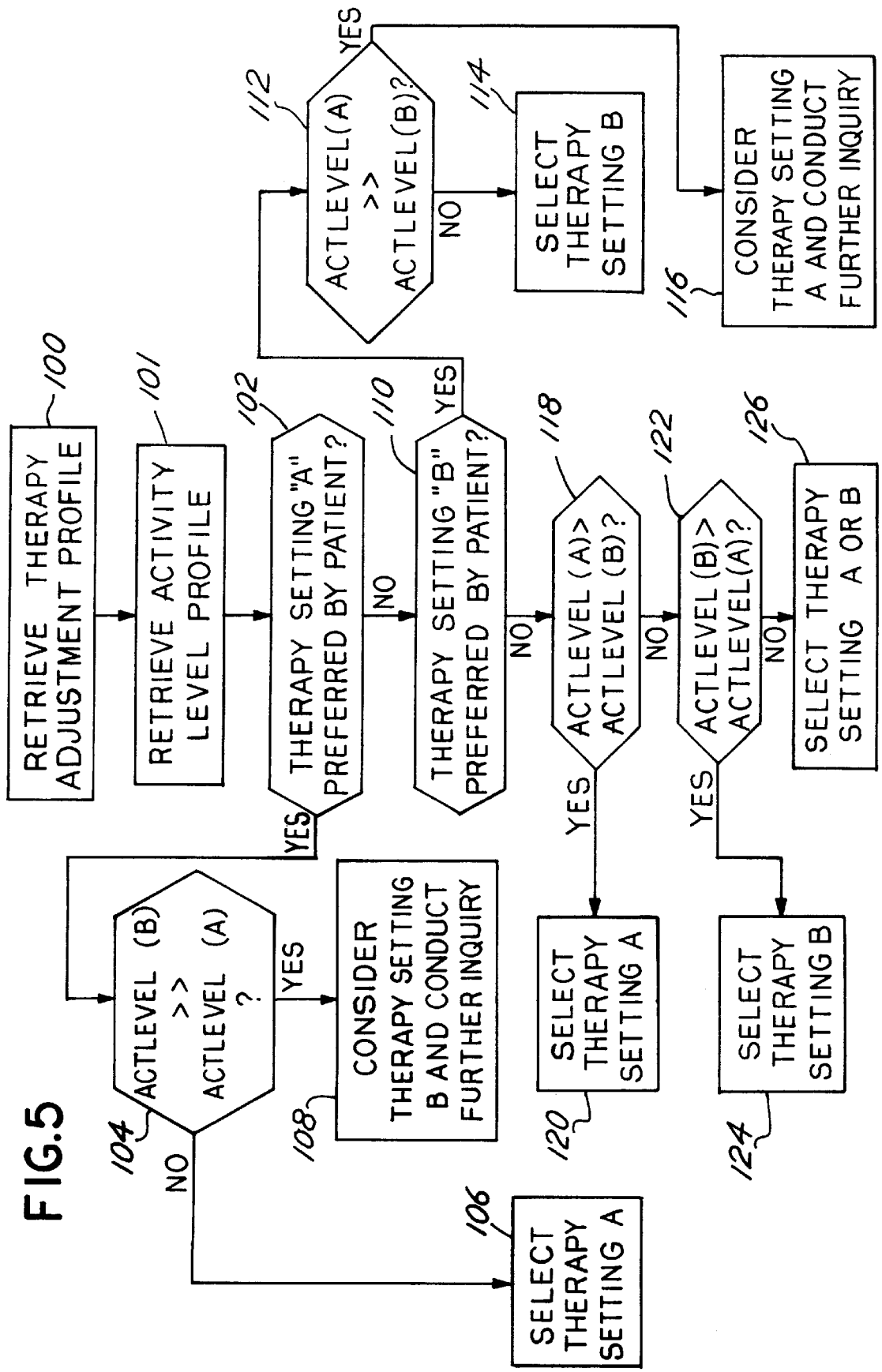
FIG. 5 is a flow diagram illustrating the steps of a process for adjusting patient therapy according to a preferred embodiment of the invention.

FIG. 5 illustrates the process steps according to a preferred embodiment of the invention by which a physician may adjust patient therapy based on the objective data provided by the patient activity level recorder and the patient therapy adjustment recorder described above. In this example, it will be assumed for simplicity that only two therapy settings where undertaken by the patient, settings "A" and "B". At steps 100 and 101, respectively, the physician retrieves the therapy adjustment profile and activity level profile through respective reporting interfaces. At step 102, the patient is interviewed to determine whether setting "A" offered more beneficial therapy. In the event that the patient characterizes setting "A" as better, the method proceeds to state 104 where the activity level profile is reviewed to determine if ACTLEVEL(A)—the general activity level corresponding to therapy setting "A"—was much less than ACTLEVEL(B)—the general activity level corresponding to therapy setting "B". If not, the physician selects therapy setting "A" as represented at state 106. If, on the other hand, ACTLEVEL(A) is much less than that ACTLEVEL(B), the method proceeds to state 108. This step would indicate that the patient undertook generally much less activity under setting "A". Thus, at state 108, the physician considers whether therapy setting "B" is more beneficial to the patient, despite the patient's indicated preference for therapy setting "A". Further inquiry may be undertaken to reconcile the increased activity level corresponding to setting "B". Thus, the patient activity level data and patient therapy adjustment level data are utilized to objectively qualify the patient's subjective preference for setting "A".

Still referring to FIG. 5, in the event that the patient, at state 102, does not indicate that therapy setting "A" is preferred, the method continues to state 110 where further inquiry is made as to the patient's preference for therapy setting "B". If such a preference is indicated, the method branches to state 112 where the activity level profile is analyzed to determine whether ACTLEVEL(A) greatly exceeds ACTLEVEL(B). If that condition is met, the physician proceeds to step 116 where consideration of therapy setting "A" is made and further inquiry is conducted to reconcile the increased activity level corresponding to activity level "A". If the condition at state 112 is not met, the physician selects therapy setting "B" at state 114.

As denoted by state 118, if neither condition at state 102 or state 110 is met, the method requires analysis of the activity level profile to determine whether ACTLEVEL(A) is greater than ACTLEVEL(B). Such a condition would indicate that the patient undertook more activity under therapy setting "A" than under therapy setting "B". In that case, therapy "A" is selected at state 120. If the condition at state 118 is not met, the activity level profile is analyzed to determine whether ACTLEVEL(B) is greater than ACTLEVEL(A) at state 122. If that condition is met, therapy setting "B" is selected at state 124. If no difference between the activity levels corresponding to respective therapy settings "A" and "B" is noticeable, then either therapy setting may be selected as denoted at state 126.

Those skilled in the art will recognize that the preferred embodiments may be altered or amended without departing from the true spirit and scope of the invention, as defined in the accompanying claims.

What is claimed is:

1. A system for obtaining objective patient data comprising:
   a recorder for recording an historical representation of patient activity levels, the recorder including:
   a sensor for generating signals corresponding to respective levels of patient activity;
   a signal processor for generating a patient activity level profile from the signals, the patient activity level profile including an historical representation of activity levels in a plurality of predetermined categories of activity and the relative amounts of time that a patient has engaged in each of the categories of activity, wherein the predetermined categories include rest, moderate and vigorous activity levels;
   a storage for storing the patient activity level profile; and
   a reporting interface for permitting a physician to retrieve the patient activity level profile;
   whereby the retrieved patient activity level profile may be used by a physician to objectively interpret subjective patient information.

2. The system according to claim 1, wherein the signal processor is adapted to categorize one of the levels of patient activity by comparing a long-term average activity level and a short-term average activity level.

3. The system according to claim 1, wherein the recorder further comprises a filter for filtering the signals.

4. The system according to claim 1, wherein the recorder further comprises a patient therapy adjustment recorder for recording a patient therapy adjustment profile representing historical adjustments of patient therapy.

5. The system according to claim 1, further comprising a patient control interface for permitting patient control of therapy.

6. A method of obtaining objective patient data comprising the steps of:
   providing a recorder for recording an historical representation of patient activity levels;

recording an historical representation of patient activity levels as a patient activity level profile, including a plurality of predetermined categories of activity and the relative amounts of time that a patient has engaged in each of the categories of activity, wherein the predetermined categories of activity comprise categories of rest, moderate and vigorous activity;

retrieving the historical representation; and utilizing the historical representation to objectively interpret subjective patient information.

7. The method according to claim 6, wherein the step of providing a recorder comprises the steps of:

providing a sensor for generating signals representing respective levels of patient activity;

providing a signal processor for generating the patient activity level profile from the signals;

providing a storage for storing the patient activity level profile; and providing a reporting interface enabling retrieval of the stored patient activity level profile from the storage.

8. The method according to claim 6, wherein the step of recording an historical representation of patient activity levels further comprises the step of categorizing patient activity in one of the predetermined categories by comparing a long-term average activity level and a short-term average activity level.

9. The method according to claim 6, further comprising the step of providing a patient therapy adjustment recorder for recording a patient therapy adjustment profile representing historical adjustments of patient therapy.

10. The method according to claim 9, wherein the step of utilizing the historical representation further comprises the step of optimizing patient therapy based on the therapy adjustment profile.

11. The method according to claim 9, wherein the step of utilizing the historical representation further comprises the step of interviewing the patient to obtain the subjective information.

12. The method according to claim 9, wherein the step of utilizing the historical representation comprises the step of choosing one of a plurality of therapy settings based on the historical representation.

13. The method according to claim 9, wherein the step of providing a therapy adjustment recorder further comprises the step of providing a patient control interface for permitting patient control of therapy.

* * * * *